United States Patent [19]
Jansen et al.

[11] Patent Number: 5,413,112
[45] Date of Patent: May 9, 1995

[54] EXPIRATORY FLOW MEASURING DEVICE

[75] Inventors: Murray L. Jansen, Porirua; Donald E. Killick, Plimmerton; Alexander Lang, Eastbourne; Royce T. Pullman, Lower Hutt; Christopher M. Sutton, Ngaio; Cornelis H. Zwaaneveld, Fairfield, all of New Zealand

[73] Assignee: Asthma International Research Limited, Wellington, New Zealand

[21] Appl. No.: 952,864

[22] PCT Filed: May 21, 1991

[86] PCT No.: PCT/GB91/00793
§ 371 Date: Jan. 15, 1993
§ 102(e) Date: Jan. 15, 1993

[87] PCT Pub. No.: WO91/17707
PCT Pub. Date: Nov. 28, 1991

[30] Foreign Application Priority Data

May 21, 1990 [NZ] New Zealand ............... 233745

[51] Int. Cl.⁶ ............................................. A61B 5/09
[52] U.S. Cl. ................................ 128/726; 73/861.75; 73/861.76; 482/13
[58] Field of Search ................... 128/726; 482/13; 73/861.75, 861.76

[56] References Cited

U.S. PATENT DOCUMENTS

| | | |
|---|---|---|
| 2,296,973 | 9/1942 | Ardelt . |
| 2,889,707 | 6/1959 | Snider . |
| 4,144,883 | 3/1979 | Grieshaber ............... 128/726 |
| 4,679,566 | 7/1987 | Tamm . |

FOREIGN PATENT DOCUMENTS

| | | |
|---|---|---|
| 1096098 | 6/1955 | France .............. 128/726 |
| 172981 | 7/1976 | New Zealand . |
| 1344836 | 1/1974 | United Kingdom . |
| 1351112 | 4/1974 | United Kingdom . |
| 2024628 | 1/1980 | United Kingdom . |
| WO89/12423 | 12/1989 | WIPO . |

*Primary Examiner*—Lee S. Cohen
*Attorney, Agent, or Firm*—Sterne, Kessler, Goldstein & Fox

[57] ABSTRACT

A device for measuring the maximum flow rate of a single forced expiration, comprises an elongated hollow body with inlet and outlet ends, a vane mounted to a shaft and rotatable within the body from a defined rest position, and an indicator to indicate maximum displacement of the vane from its rest position. The vane is shaped such that airflow from the inlet end past the vane causes the vane to rotate away from the rest position with the plane of rotation preferably being at about 90° to the airflow through the elongated body.

19 Claims, 3 Drawing Sheets

EXPIRATORY FLOW MEASURING DEVICE

TECHNICAL FIELD

This invention relates to an expiratory flow measuring device. More particularly, it relates to a device for measuring the maximum flow rate of a single forced expiration.

BACKGROUND

Recent investigations into the causes of death from asthma in the community have suggested that major problems exist in the management of this common disorder. Although several factors have been identified that may contribute to death, the single most important one is a failure, not only by the patient and relative but also by the doctor, to assess and appreciate the severity and speed of onset of an acute attack, resulting in delay in initiating appropriate treatment. An explanation that could account for this observation is that symptoms alone are commonly used to assess the severity of an asthma attack, despite studies having established this approach as inadequate (Burdon J. G. W, et al, "The Perception of Breathlessness in Asthma", *Am Rev Respir Dis*, 126:825-828 (1982)). The studies found that some asthmatic patients may be symptomless in the presence of substantial air flow limitation and that patients with the most reactive airways commonly exhibit minimal symptoms during an asthma attack.

The above findings suggest that regular assessment of airflow obstruction by objective means is necessary for appropriate management of these patients. One such objective assessment is a measurement of peak expiratory flow (ie. the maximum flow rate of a single forced expiration).

A variety of mechanical devices for measuring the maximum flow rate of a single forced expiration have been proposed to date. By way of example reference should be made to New Zealand Patent Specification No. 172981 (Allen & Hanburys) and to British Patent Specification Nos 1344836 and 1351112 (Ferraris Development) which describe such devices. Further and particular reference should also be made to British Patent Specification No. 1463814 and U.S. Pat. No. 3,958,565 which describe the ventilatory capacity measuring instrument developed by B. M. Wright, conventionally known as the Wright peak low meter.

However, most if not all of these prior art devices suffer from the disadvantages that they are less than accurate over the full range of expiratory flow rates. Moreover, such devices tend to be bulky and relatively large in size. In consequence, they are not generally carried by asthmatics.

It is an object of the present invention to provide a device for measuring peak expiratory flow which goes some way towards overcoming the above disadvantages or which at least provides the public with a useful choice.

SUMMARY OF THE INVENTION

Accordingly, the present invention may broadly be said to consist in an expiratory flow measuring device for measuring the maximum flow rate of a single forced expiration comprising:

an elongated hollow body having an inlet end and an outlet end;

a shaft mounted within the body between the inlet and outlet ends thereof;

a vane mounted to said shaft and rotatable within said body away from a defined rest position, said vane being shaped such that airflow through the body from the inlet end past the vane causes the vane to be rotatably displaced from said rest position; and indicator means co-operable with the vane to indicate the extent of maximum displacement of the vane from the rest position.

In a preferred embodiment, the body of the device is substantially tubular.

In a further preferred embodiment, the shaft is mounted substantially parallel to the longitudinal axis of the body with said vane being rotatable thereabout. The plane of rotation of the vane about the shaft is therefore at substantially 90° to both the longitudinal axis of the body and the direction of airflow through the body.

It is still further preferred that the device include a baffle positioned within the body intermediate the inlet end of the body and the vane, which baffle is provided to direct the airflow into a generally annular volume within the body.

The device can also conveniently include biasing means to urge the vane towards its rest position.

Preferably, the device includes a mouthpiece engageable with the inlet end of the body and through which air expired by a patient can pass into the body.

BRIEF DESCRIPTION OF THE DRAWINGS

While the invention is broadly as defined above, it will be appreciated by those persons skilled in the art that it also includes the embodiments of which the following description provides examples. More particularly, the invention includes the preferred embodiments of the invention illustrated in the accompanying drawings in which.

DESCRIPTION OF THE INVENTION

The present invention relates to a device for reliably and accurately measuring the peak expiratory flow rate of a patient with asthma in order to provide the patient with an objective assessment of airway obstruction. This assessment, particularly during an asthma attack, allows the patient to monitor the severity of the attack and to determine the appropriate action to be taken. This action may involve the self-application of a predetermined dosage of asthma medication or, in the case of a severe attack, the seeking of urgent medical assistance.

Figure 1:
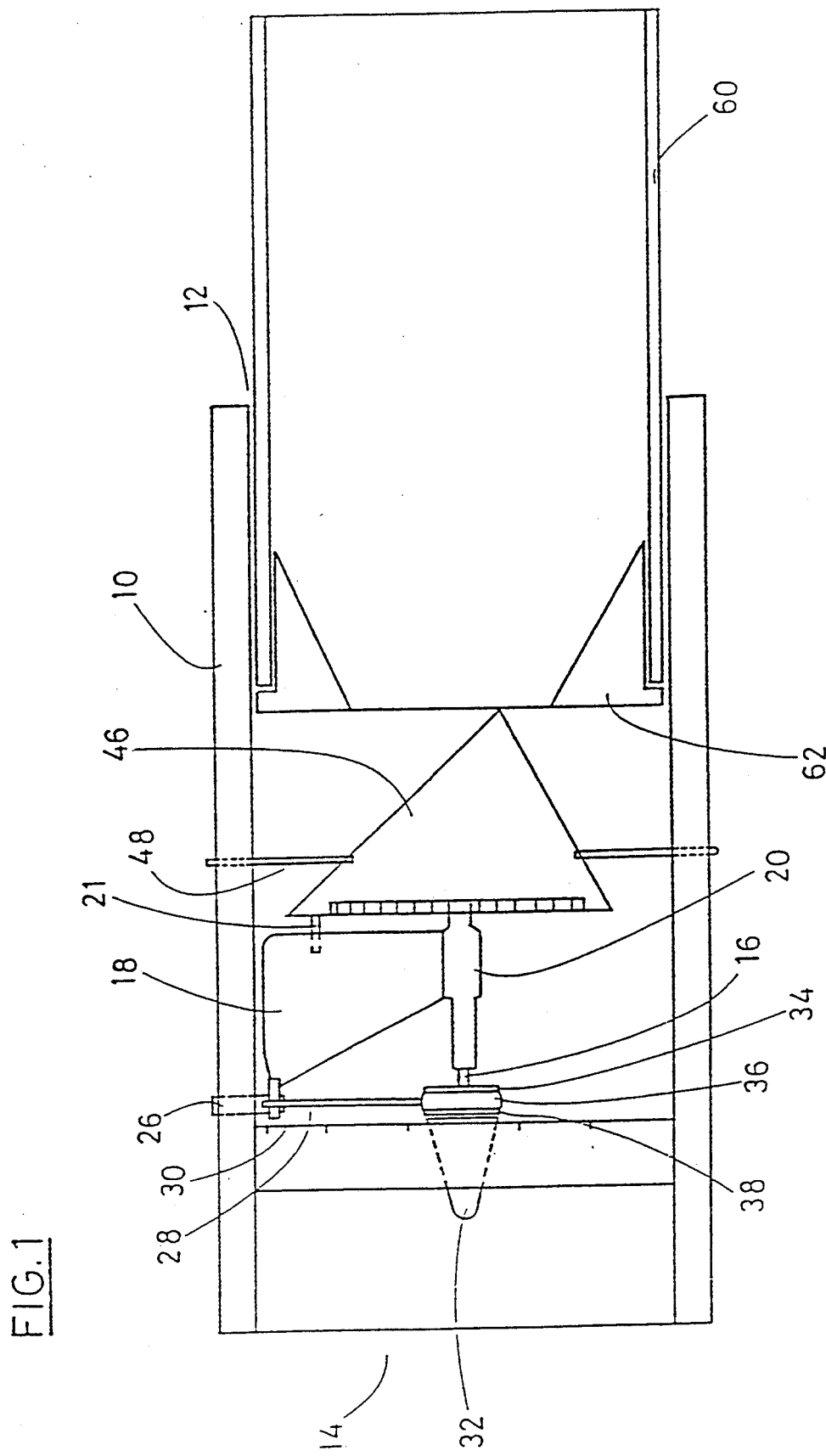
FIG. 1 is a side elevational view partly in section of a preferred form of the device
Figure 2:
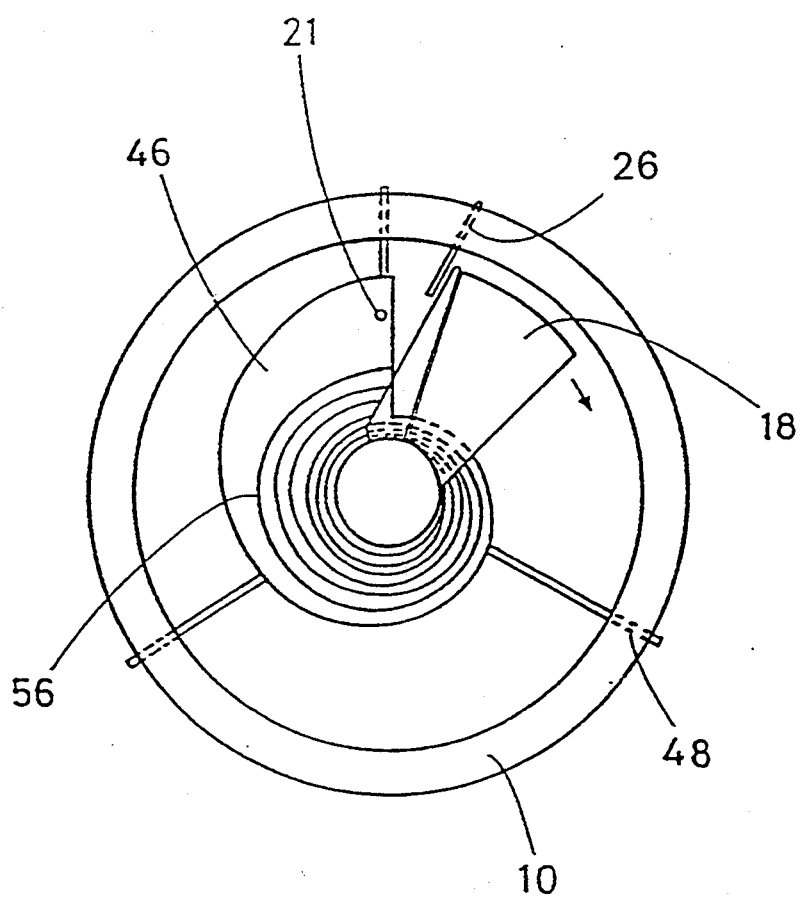
FIG. 2 is an elevational view of the device of FIG. 1 from the outlet end

The first component of the device is an elongated hollow body. As shown in FIGS. 1 and 2 of the accompanying drawings it is preferred that this body 10 be substantially tubular. However, other appropriate shapes for the body are in no way intended to be excluded.

Body 10 has an inlet end 12 and an outlet end 14. Between inlet end 12 and outlet end 14 there is provided a shaft 16 which is preferably disposed substantially parallel to the longitudinal axis of body 10.

Figure 3:
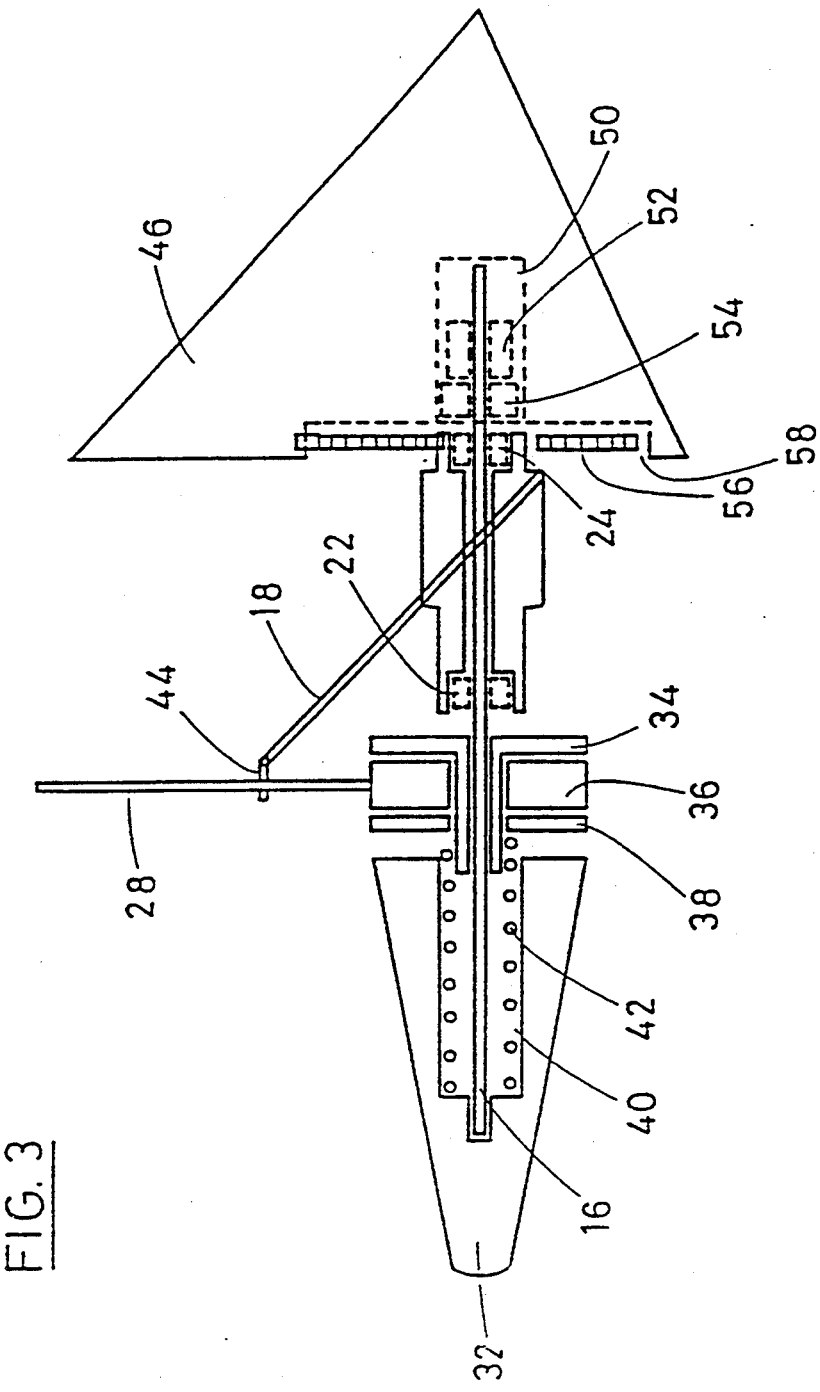
FIG. 3 is a detail of various components of the device of FIG. 1.

A vane 18 is carried by shaft 16 and is rotatable within the body. As shown in FIG. 3, this rotatability is achieved through the mounting of vane 18 to hub 20 which is itself rotatable about shaft 16. Conveniently, retarding friction when hub 20 and in turn vane 18 are rotating about shaft 16 is minimised by the provision of bearings 22 and 24.

Vane 18 is shaped such that airflow through body 10 from inlet end 12 causes vane 18 to be rotatably displaced from a defined rest position. Conveniently, this is achieved by orienting the plane of vane 18 at about 45° to the longitudinal axis of body 10.

The rest position of the vane can be defined by any suitable means. By way of example, as shown in FIGS. 1 and 2, the rest position of the vane is defined by a stop 26.

The device of the invention further includes indicator means to indicate the extent of the displacement of the vane from its rest position. The indicator means is co-operable with the vane of the device to indicate the peak angular displacement of the vane.

Conveniently, as shown in the accompanying drawings, the indicator means comprises a radial pointer 28 which is again carried by shaft 16 and which is associated with a circumferential scale 30 provided on the internal surface of tubular body 10. Scale 30 is appropriately graduated to indicate the extent of airway restriction for the patient using the device.

It is preferred that the indicator means be resettable to a zero position which corresponds to the rest position of vane 18. To this end, the indicator means further includes manual reset means the form of a knob 32.

Details of the construction of the indicator means are shown in FIG. 3. As illustrated, shaft 16 is provided at one end with knob 32 and associated retaining ring 34 which are both fixed to the shaft. A pointer-bearing ring 36 carrying pointer 28 and a friction ring 38 are also provided which turn freely on the shaft 16.

Within knob 32 there is a bore 40 which houses a cylindrical pressure spring 42 which presses lightly against friction ring 38. The extent of movement of spring 42 is limited by the retaining ring 34 attached to shaft 16.

Radial pointer 28 and vane 18 are made co-operable through the engagement of the pointer and the trailing edge of the vane. In this way, rotation of vane 18 from its rest position causes pointer 28 to be similarly rotated from its zero position to a position on circumferential scale 30. As shown, this engagement between vane 18 and pointer 28 is preferably achieved by provision of a tab 44 on the trailing edge of the vane. This is of course not critical as vane 18 could directly engage pointer 28 or alternatively tab 44 could be provided on the pointer itself.

In a preferred embodiment of the .invention the device further includes a baffle. When included, the baffle is positioned within the body between the inlet end and the vane and is shaped to direct airflow into a generally annular volume within the body. Directing the airflow in this way increases the efficiency of operation and accuracy of the device.

As shown in the drawings, baffle 46 is preferably of a general conical shape to reduce turbulence with the apex of the cone towards the inlet end 12 of the body 10. Conveniently, baffle 46 is mounted within the body 10 by three pegs 48 which are equidistantly spaced around the inner diameter of body 10 and which are of dimensions so as to not substantially disrupt the airflow through the body.

In the presently most preferred form, baffle 46 provides the mounting for shaft 16. Details of this mounting are shown in FIG. 3.

As illustrated, one end of shaft 16 is secured within a bore 50 within the baffle 46 by retaining bush 52. There is further provided within bore 50 a bearing 54 to allow the shaft 16 to rotate as necessary.

It is particularly preferred that baffle 46 be shaped such that as vane 18 turns, progressively less area of the vane is exposed to the airflow. This is conveniently achieved by providing baffle 46 with its basal section describing a spiral plane as shown in FIG. 2. This shaping of the baffle is for reasons of sensitivity and coverage of an appropriate range of airflows as will be described be low.

In a particularly preferred embodiment of the invention, biasing means are provided to urge the vane towards its rest position at stop 26. The biasing means is conveniently a hair spring 56 although this is not critical.

Where biasing means in the form of hair spring 56 are provided, the spring is conveniently located within an appropriate recess 58 provided in the base of baffle 46 with the ends of the spring being attached to hub 20 and baffle 46 respectively.

Whereas the rest position of vane 18 is defined by stop 26 the point of maximum possible angular displacement from the rest position is preferably also defined. By way of example and as shown in FIGS. 1 and 2 this is achieved through the provision of a stop 21 on baffle 46 which is co-operable with the trailing edge of vane 18.

Conveniently, the device of the invention includes a mouthpiece through which a patient can blow. This mouthpiece is preferably releasably engageable with the inlet end 12 of the body 10 of the device for reasons of hygiene.

As is shown in FIG. 1, the mouthpiece 60 is a substantially tubular hollow body of a similar albeit slightly reduced diameter compared to that of body 10, the external surface of mouthpiece 60 being slidably engageable with the internal surface of body 10. Conveniently, the end of mouthpiece 60 which engages body 10 is provided with flow directing means in the form of annular deflector 62. This deflector is included to centrally direct the airflow onto baffle 46.

In addition, the location of the deflector 62 with respect to the baffle 46 may be adjusted in order to cover different ranges of airflow according, for example, to the needs of a particular user group.

The operation of the preferred form of the invention will now be described.

The position of pointer 28 is checked by the patient and if necessary adjusted to the scale zero by turning knob 32. Vane 18 is already at its rest position against stop 26 due to the action of spring 56.

The patient places his or her mouth around mouthpiece 60 and blows through the mouthpiece into body 10. The flow of air past vane 18 causes it to turn, thereby also pushing pointer 28 to the position of maximum angular displacement of the vane. By virtue of the slight friction experienced by pointer-bearing ring 36 on shaft 16, the pointer 28 stays at the position of maximum displacement. Meanwhile, vane 18 returns to its rest position against stop 26 due to spring 56.

The patient can then obtain an objective assessment of the extent of his or her airway obstruction from a comparison of the position of pointer 28 with graduated scale 30.

By way of demonstration of the operation of the device of the invention the variability of this device was compared with a Wright Peak Flow Meter. The device was connected in series with the Wright Peak Flow Meter so that the maximum flow rate during forced expiration was simultaneously measured on both instruments.

One investigator undertook 133 consecutive expiratory manoeuvres with different degrees of effort to achieve a range of values recorded on the Wright Peak Flow Meter from 75 to 655 liters per minute. A comparison of paired values obtained with the new device and the Wright Peak Flow Meter was undertaken and demonstrated a correlation coefficient ($\Gamma$) of 0.99.

No change in calibration was observed with the present device with repeated measurements. This comparison demonstrates that the new device provides an accurate method for determining maximum expiratory flow comparable to that of the Wright Peak Flow Meter.

Thus, in accordance with the present invention, there is provided a peak expiratory flow measuring device which will quickly and accurately provide a patient with an objective assessment of the obstruction of his or her airway. This is particularly useful during an asthma attack as it will enable the patient to assess the severity of the attack and to take the necessary steps depending on the assessment obtained. This will be an invaluable aid to the patient in self-monitoring his or her condition.

In its preferred forms, the device of the invention is particularly accurate and sensitive over a range of expiratory flow rates due to the provision and shape of the baffle. More particularly, the sensitivity of the device is greatest at low flow rates due to the exposure of almost the entire area of the vane to the airflow whereas at greater flow rates a progressively decreasing area of the vane is exposed. In this way a wide range of airflows can be measured without losing the desirably sensitive measurement of low airflows.

The device of the invention also has the most important advantage of being able to function effectively when made of a comparable size to a conventional inhaler. This small size of the device makes it truly portable in the sense of being able to be carried in a pocket or purse of a patient. This portability will enable the patient to carry the device without the inconvenience associated with other larger and heavier devices which will mean that the present device is much more likely to be at hand whenever and wherever the patient suffers an asthma attack. This continual availability of the device is essential to any self-management programme the patient may follow.

It will be appreciated that the above description is provided by way of example only and that the invention is not limited in scope thereto.

We claim:

1. An expiratory flow measuring device for measuring a maximum flow rate of a single forced expiration, comprising:
   an elongated hollow body having an inlet end and an outlet end;
   a shaft mounted within the body between the inlet and outlet ends;
   a vane mounted to said shaft and rotatable within said body away from a rest position, said vane being shaped such that airflow through the body from the inlet end past the vane causes the vane to be rotatably displaced from said rest position; and
   indicator means co-operable with the vane to indicate a maximum displacement of the vane from the rest position, said indicator means comprising a radial pointer carried by said shaft and an associated graduated scale provided on an internal surface said body and against which a relative position of said pointer can be read.

2. A device according to claim 1 wherein the shaft is mounted within the body substantially parallel to a longitudinal axis thereof, a plane of rotation of the vane being at substantially 90° to both the longitudinal axis of the body and a direction of airflow through the body.

3. A device according to claim 1 wherein said vane is substantially planar, a plane of the vane being oriented at about 45° to a longitudinal axis of the body.

4. A device according to claim 1, further comprising a stop mounted on the body, wherein said rest position is defined by the stop to prevent 360° rotation of said vane within said body.

5. A device according to claim 1, further comprising: biasing means biasing said vane towards the rest position.

6. A device according to claim 5 wherein said biasing means is a spring.

7. A device according to claim 1 wherein said body is substantially tubular.

8. A device according to claim 1 wherein position zero on said scale corresponds to the rest position of the vane.

9. A device according to claim 8 wherein said indicator means and said vane are co-operable through engagement of said pointer with said vane, such that during rotation away from the rest position the vane carries the pointer away from position zero on said scale.

10. A device according to claim 9 wherein the engagement between the pointer and the vane is effected through provision of a pointer-engaging tab on a trailing edge of said vane.

11. A device according to any one of claims 8 to 10 further comprising: manual reset means to allow manual resetting of the pointer to position zero on said scale.

12. A device according to claim 1, further comprising: a baffle mounted within said body between the inlet end and the vane, said baffle being shaped to direct airflow from the inlet end into a generally annular volume within said body.

13. A device according to claim 12 wherein said baffle is substantially conical in shape.

14. A device according to claim 13 wherein said substantially conical baffle has a basal section which describes a spiral plane.

15. A device according to claim 12, further comprising:
   a mouthpiece releasably engaging the inlet end of said body.

16. A device according to claim 15, wherein said mouthpiece comprises:
   airflow directing means to direct airflow substantially centrally onto said baffle.

17. A device according to claim 1, further comprising:
   a mouthpiece releasable engaging the inlet end of said body.

18. A device according to claim 7, further comprising:

a baffle mounted within said elongated hollow body, and wherein said mouthpiece comprises an airflow directing means to direct airflow substantially centrally onto said baffle.

19. An expiratory flow measuring device for measuring a maximum flow rate of a single forced expiration, comprising:

an elongated hollow body having an inlet end and an outlet end;

a shaft mounted within the body between the inlet and outlet ends;

a vane mounted to said shaft and rotable within said body away from a rest position, said vane being shaped such that airflow through the body from the inlet end past the vane causes the vane to be rotably displaced from said rest position;

indicator means co-operable with the vane to indicate a maximum displacement of the vane form the rest position; and a baffle mounted within said body between the inlet end and the vane, said baffle being shaped to direct airflow from the inlet end into a generally annular volume within said body, said baffle having a substantially conical shape and a basal section defining a spiral plane.

* * * * *